United States Patent [19]

Beideman et al.

[11] Patent Number: 5,632,764
[45] Date of Patent: May 27, 1997

[54] SNAP FIT COLLAR FOR COUPLING THE END OF A FLEXIBLE COIL TO THE ACTUATOR OR CLEVIS OF AN ENDOSCOPIC SURGICAL INSTRUMENT AND AN ENDOSCOPIC SURGICAL INSTRUMENT INCORPORATING THE SAME

[75] Inventors: Tracie L. Beideman, Pembroke Pines; Gary R. Dill, Lauderhill; Kevin F. Hahnen, Cooper City; Thomas O. Bales, Coral Gables, all of Fla.

[73] Assignee: Symbiosis Corporation, Miami, Fla.

[21] Appl. No.: 389,758

[22] Filed: Feb. 15, 1995

Related U.S. Application Data

[63] Continuation-in-part of Ser. No. 275,291, Jul. 14, 1994, Pat. No. 5,478,350.
[51] Int. Cl.$^6$ ................................................. A61B 17/00
[52] U.S. Cl. ................................................. 606/205; 128/751
[58] Field of Search ................................ 606/51, 52, 170, 606/174, 205–211; 128/750–755

[56] References Cited

U.S. PATENT DOCUMENTS 5,152,779  10/1992  Sanagi .
5,228,451  7/1993  Bales et al. .......................... 606/205
5,336,238  8/1994  Holmes et al. .

*Primary Examiner*—Michael Buiz
*Assistant Examiner*—William Lewis
*Attorney, Agent, or Firm*—David P. Gordon

[57] ABSTRACT

A snap-fit collar for coupling the end of a flexible coil to a part of an endoscopic instrument is a substantially cylindrical member having a first end portion with a stop flange, a resilient tapered locking flange spaced apart from the stop flange defining a waist or groove between the stop flange and the locking flange, and second end portion having a pair of cantilevered substantially semi-cylindrical legs. The first end portion is preferably frustroconical and flares diametrically outward to form the stop flange which has a first diameter. The waist or groove has a second diameter which is smaller than the first diameter. The tapered locking flange is also preferably frustroconical and tapers diametrically inward from a third diameter which is larger than the second diameter. Each of the legs is inclined diametrically outward and includes a plurality of coil engaging ribs on its inner surface. The outer surface of each leg is preferably provided with a longitudinal key and the free end of each leg is preferably tapered radially inward. The collar has a throughbore which extends through the first end portion to the space between the legs. An endoscopic instrument actuator and a clevis for use with the snap-fit collar each include a throughbore having a step and a pair of diametrically opposed keyways which extend into at least a portion of the throughbore wall.

21 Claims, 5 Drawing Sheets

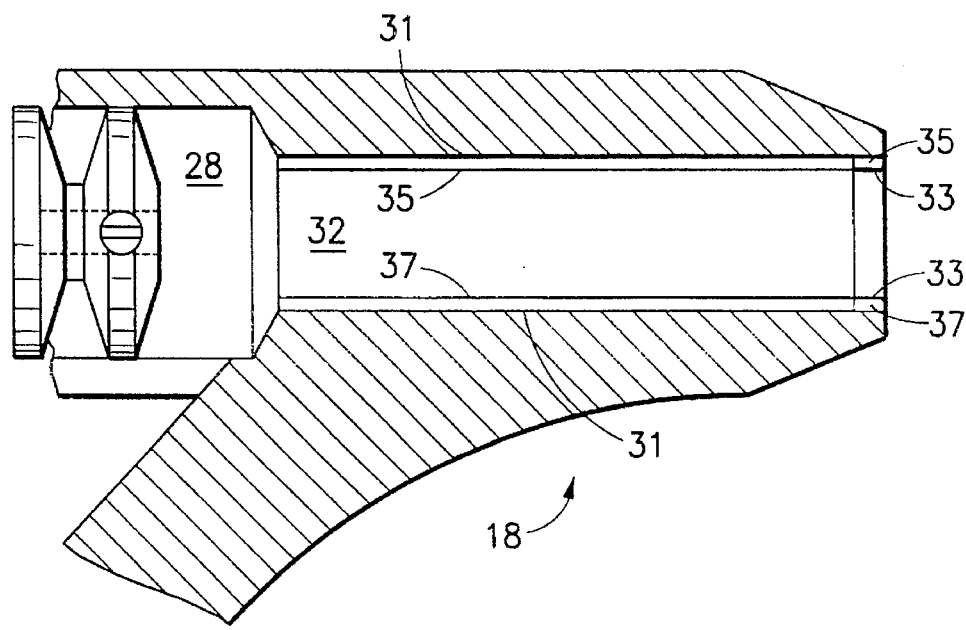
FIG. 3
FIG. 3a
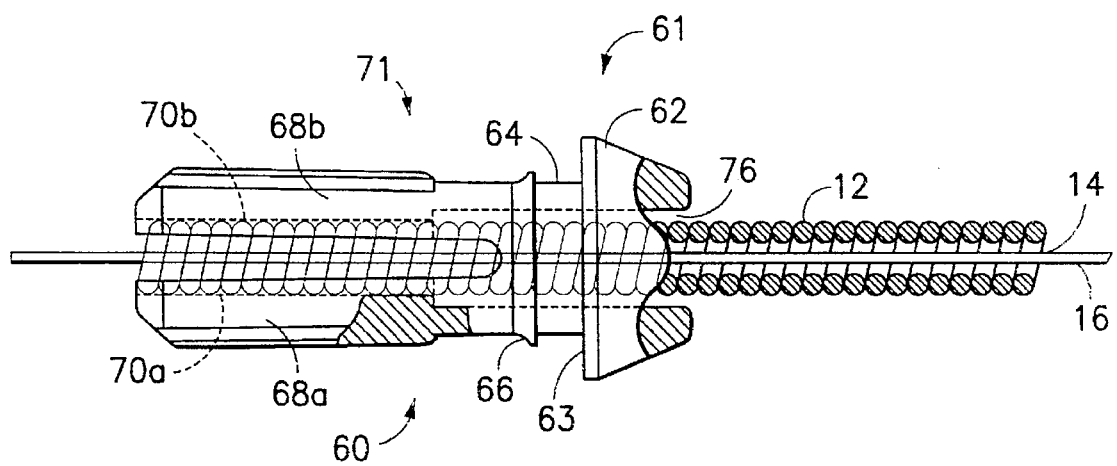
FIG. 4

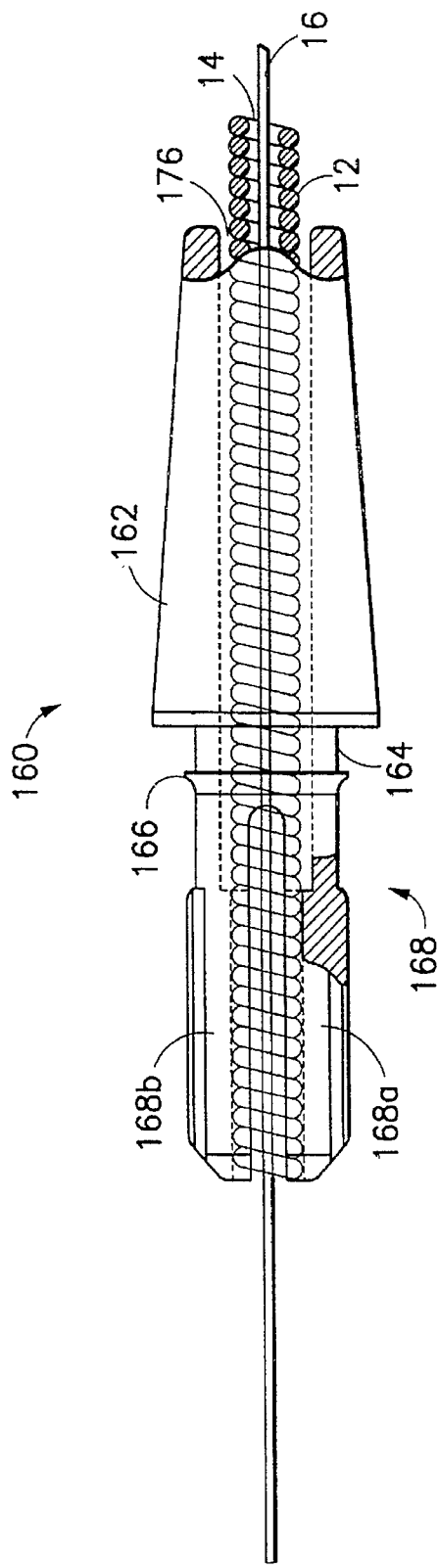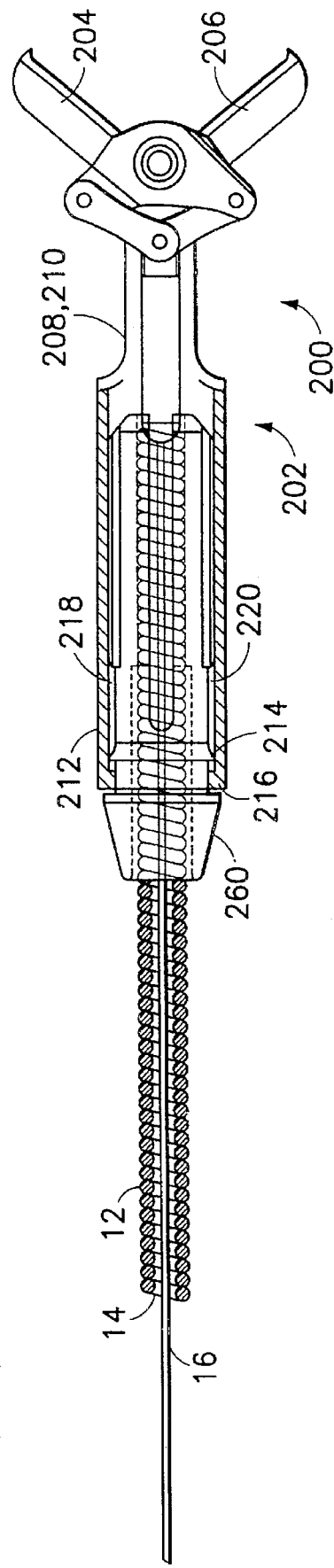

5,632,764

SNAP FIT COLLAR FOR COUPLING THE END OF A FLEXIBLE COIL TO THE ACTUATOR OR CLEVIS OF AN ENDOSCOPIC SURGICAL INSTRUMENT AND AN ENDOSCOPIC SURGICAL INSTRUMENT INCORPORATING THE SAME

This application is a continuation-in-part of application Ser. No. 08/275,291 filed Jul. 14, 1994 now U.S. Pat. No. 5,478,350 the complete disclosure of which is hereby incorporated by reference herein.

BACKGROUND OF THE INVENTION

1. Field of the Invention

The invention relates to endoscopic surgical instruments which have a proximal actuator and distal end effectors which are coupled to each other by a flexible coil. More particularly, the invention relates to a snap-fit collar for coupling the end of a flexible coil of an endoscopic instrument to the actuator or to the end effectors of the instrument.

2. State of the Art

Endoscopic surgical instruments generally include a hollow tube member having a proximal end and a distal end and a control member such as a push rod or a pull wire which extends through and is reciprocally movable in the tube member. An actuator mechanism is coupled to the proximal ends of the tube and control member, and at least one of a pair of end effectors is coupled to the distal end of the tube and control member by means of a clevis. Operation of the actuator mechanism causes the control member to move relative to the tube member which in turn causes the end effector to rotate in the clevis. The hollow tube member is often a flexible coil which permits the end effectors of the instrument to be fed through a curved or tortuous path to the surgical site. The coupling of the flexible coil to the clevis and to the actuator mechanism is most often effected by crimping.

Parent application Ser. No. 08/275,291 discloses an actuator mechanism for an endoscopic instrument which includes a stationary handle having a stepped throughbore with a relatively smaller diameter at the distal end and a relatively larger diameter at the proximal end. A cylindrical rack member is slidably disposed in the larger diameter portion of the throughbore. The larger diameter portion of the throughbore has a lower slot opening, and a movable lever is pivotally coupled to the stationary handle and is provided with a toothed upper pinion which enters the slot in the larger diameter portion of the throughbore and engages the rack member. The actuator mechanism is particularly well suited for use in an endoscopic instrument having a flexible coil tube member and a control member extending through the flexible coil. The proximal ends of the control member and the flexible coil are coupled to the actuator mechanism which imparts reciprocal movement to the control member relative to the flexible coil. The distal end of the flexible coil is coupled to a clevis within which a pair of end effectors are rotatably mounted; and the distal end of the control member is coupled to the end effectors. Several different means for coupling the ends of the flexible coil to the handle and the clevis are disclosed in the parent application, including the use of a staple and press-fit ferrule. While these couplings are effective, their assembly is time consuming and increases the cost of manufacture of the instrument.

SUMMARY OF THE INVENTION

It is an object of the invention to provide an improved means for coupling the proximal end of a flexible coil tube member to an endoscopic instrument actuator.

It is also an object of the invention to provide an endoscopic instrument actuator which is easily coupled to the proximal end of a flexible coil tube member.

It is another object of the invention to provide a coupling member which cooperates with an endoscopic instrument actuator and facilitates coupling the proximal end of a flexible coil tube member to the endoscopic instrument actuator.

It is a further object of the invention to provide an improved means for coupling the distal end of a flexible coil tube member to an endoscopic instrument clevis.

Another object of the invention to provide an endoscopic instrument clevis which is easily coupled to the distal end of a flexible coil tube member.

In accord with these objects which will be discussed in detail below, a snap-fit collar according to the invention is a molded, resilient plastic, substantially hollow cylindrical member having first and second end portions. The first end portion of the member has an interior throughbore and includes an exterior stop flange and a tapered locking flange which is spaced therefrom, with the stop flange and the locking flange defining a narrow waist portion or groove. The second end portion includes a pair of substantially semi-cylindrical resilient cantilevered legs which are spaced and diverge from each other as they extend away from the first end portion; the space between the legs being in communication with the throughbore. The first end portion is preferably frustroconical and flares diametrically outward from the first end of the member to form the stop flange which has a first diameter. The narrow waist portion has a second diameter which is smaller than the first diameter. The tapered locking flange is also preferably frustroconical and tapers diametrically inward toward the second end portion of the member from a third diameter which is larger than the second diameter. Each of the legs preferably includes a plurality of coil engaging ribs on its inner surface. The outer surface of each leg is preferably provided with a raised longitudinal key and the free end of each leg is preferably tapered radially inward.

An endoscopic instrument actuator for use with the snap-fit collar includes a throughbore having a diameter substantially the same as or slightly larger than the diameter of the tapered locking flange of the collar, and a distal step defining an opening having a diameter smaller than the diameter of the tapered locking flange, but substantially the same as or slightly larger than the diameter of the groove. The distal step is preferably provided with a pair of diametrically opposed keyways which extend into at least a portion of the throughbore wall.

An endoscopic instrument clevis for use with the snap-fit collar includes a throughbore having a diameter substantially the same as or slightly larger than the diameter of the tapered locking flange of the collar, and a proximal step defining an opening having a diameter smaller than the diameter of the tapered locking flange but substantially the same as or slightly larger than the diameter of the groove. The proximal step is preferably provided with a pair of diametrically opposed keyways which extend into at least a portion of the throughbore wall.

The snap-fit collar according to the invention fits easily over the end of a flexible coil so that its second end is substantially aligned with the end of the coil. When used to couple the coil to an actuator or a clevis, the collar and coil assembly is inserted into the end of the throughbore of the actuator or clevis with the keys on the legs of the collar engaging the keyways of the step in the throughbore. As the legs enter the throughbore they are forced radially inward towards each other and their inner coil engaging ribs engage and press into the spaces between the turns of the flexible coil where they are deformed by the coil. As the collar and coil assembly is further advanced into the throughbore, the locking flange portion passes over the step in the throughbore. Since the locking flange portion is tapered toward the second end of the collar, and the collar is made of resilient plastic, the locking flange is slightly deformed as it passes over the step into the throughbore but returns substantially to its original shape after it passes over the step. Since the diameter of the locking flange portion is larger than the diameter of the opening defined by the step, the collar is prevented from moving back over the step. The keyways in the step portion preferably extend into the wall of the throughbore a sufficient length so that the keys on the legs of the collar reside in the keyways and prevent the collar from rotation. The stop flange on the collar prevents the collar from entering further into the throughbore.

Additional objects and advantages of the invention will become apparent to those skilled in the art upon reference to the detailed description taken in conjunction with the provided figures.

BRIEF DESCRIPTION OF THE DRAWINGS

FIG. 3 is an enlarged broken side elevation view, in partial section, of the distal end of the actuator of FIG. 1 and the collar of FIG. 2 prior to assembly;

FIG. 3a is distal end view of the actuator of FIG. 3;

FIG. 4 is an enlarged broken side elevation view, partially transparent and in partial section, of the proximal ends of a coil and pull wire with the collar according to the invention attached to the proximal end of the coil;

FIG. 6 is an enlarged broken side elevation view, partially transparent and in partial section, of an alternate embodiment of the snap-fit collar of FIG. 2 having an integral strain relief sleeve; and FIG. 7 is an enlarged broken side elevation view, partially transparent and in partial section, of a snap-fit collar and clevis according to the invention.

DETAILED DESCRIPTION OF THE PREFERRED EMBODIMENTS

Figure 1:
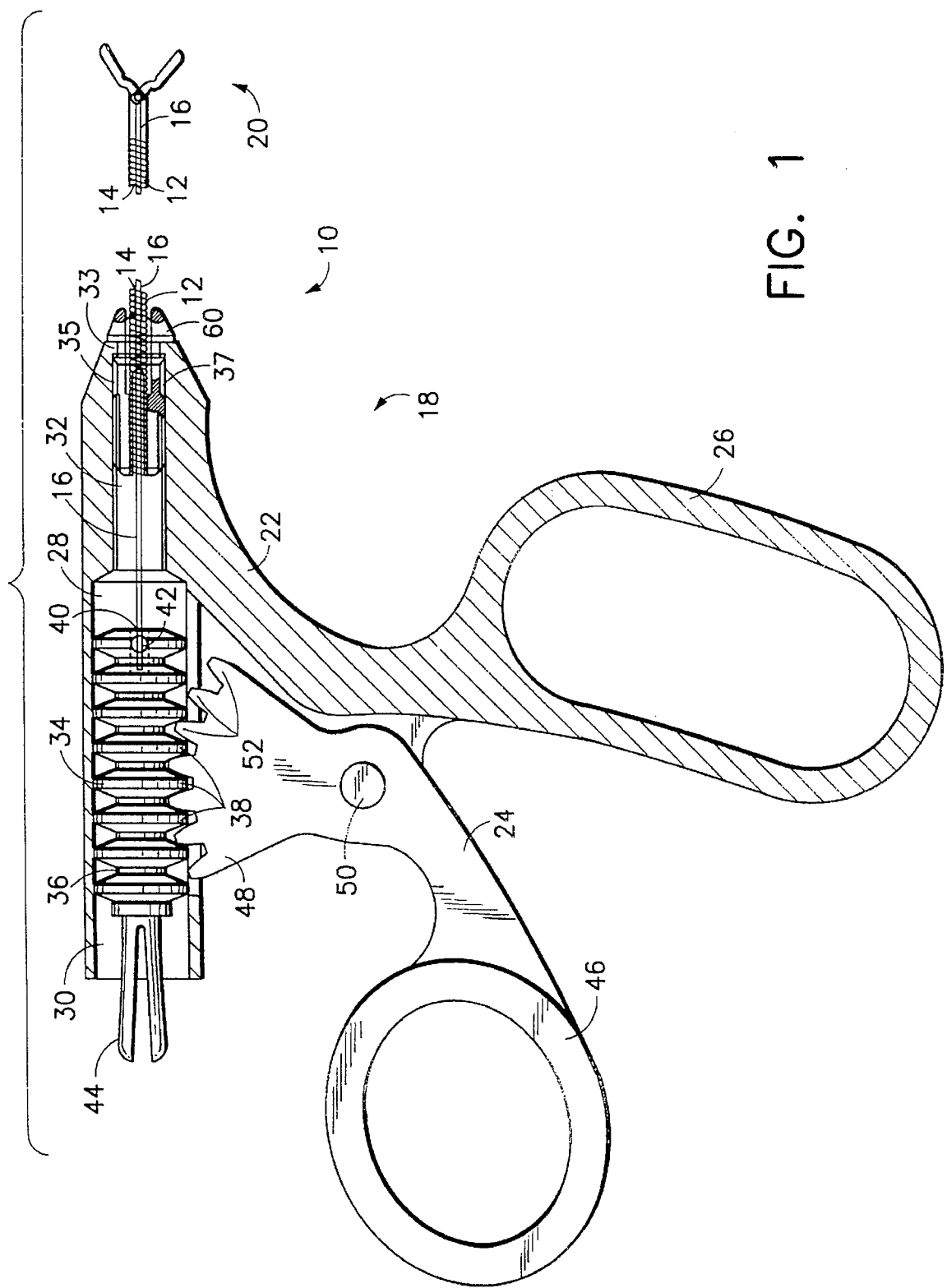
FIG. 1 is a broken side elevation view, partially transparent and in partial section, of an endoscopic instrument having an actuator handle which is coupled to a flexible coil with a snap-fit collar according to the invention.

Referring now to FIG. 1, an endoscopic forceps 10 according to the invention includes a flexible coil 12 which defines a lumen 14, a push rod or pull wire 16 extending through the lumen 14, a proximal actuator mechanism 18 coupled to the proximal ends of the coil 12 and the push rod 16 for imparting reciprocal movement to the push rod relative to the coil, and a distal end effector assembly 20 coupled to the distal ends of the coil 12 and the push rod 16. The end effector assembly 20 is responsive to reciprocal movement of the push rod 16 relative to the coil 12.

The actuator mechanism 18, according to a preferred embodiment of the invention, includes a stationary handle 22 and a movable lever 24. The stationary handle 22 has a lower finger ring 26 and an upper stepped throughbore 28. The stepped throughbore 28 has a larger diameter proximal portion 30 and a smaller diameter distal portion 32. The larger diameter portion 30 is provided with a lower slot opening 31 and the smaller diameter portion 32 is provided with a distal step 33 and a pair of diametrically opposed keyways 35, 37 which extend through the step 33 to the exterior of the stationary handle 22. A cylindrical rack member 34 is slidably disposed in the larger diameter portion 30. The rack member 34 has a cylindrical shaft 36 and a plurality of spaced apart cogs 38. The distal end of the rack member 34 is provided with a longitudinal bore 40 for receiving the rod or wire(s) 16, and a radial bore for accommodating a radial set screw 42 which enters the longitudinal bore 40 for holding the rod or wire(s) therein. The proximal end of the rack member 34 is preferably provided with an electrical connector such as a banana clip 44 for connection to a source of cautery current (not shown).

The movable lever 24 of the actuator mechanism 18 has a lower thumb ring 46 and an upper pinion 48. The movable lever 24 is coupled to the stationary handle 22 by a pivot axle 50 and is arranged so that the upper pinion 48 enters the larger diameter portion 34 of the throughbore 28 through the lower slot opening 31. The upper pinion 48 is curved and has a plurality of spaced apart teeth 52. The teeth 52 engage the spaces between the cogs 38 on the rack member 34 as seen in FIG. 1. From the foregoing, those skilled in the art will appreciate when the movable lever 24 is rotated about the pivot axle 50, the pinion 48 imparts a true linear reciprocal motion to the rack member 34.

Figure 2:
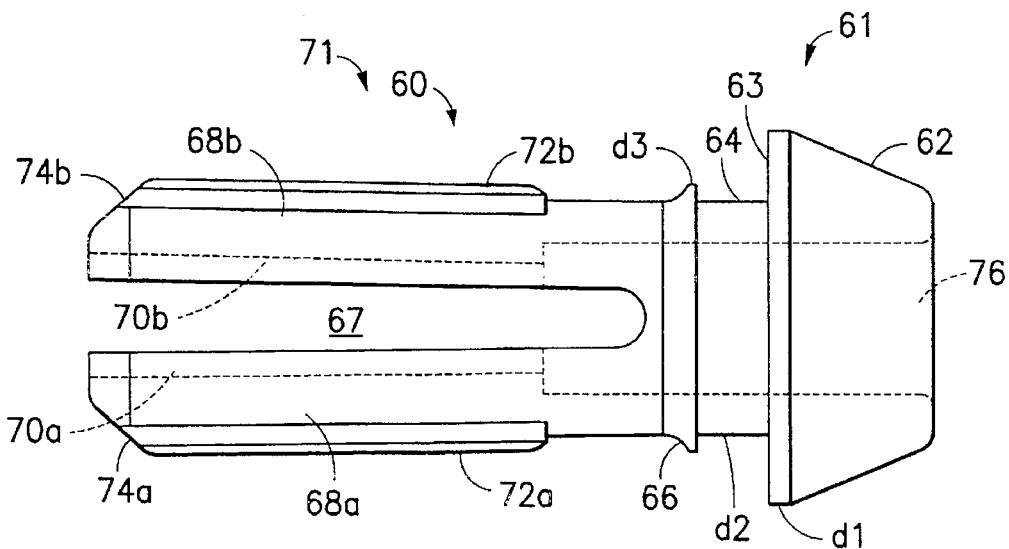
FIG. 2 is an enlarged side elevation view of a snap-fit collar according to the invention.
Figure 2A:
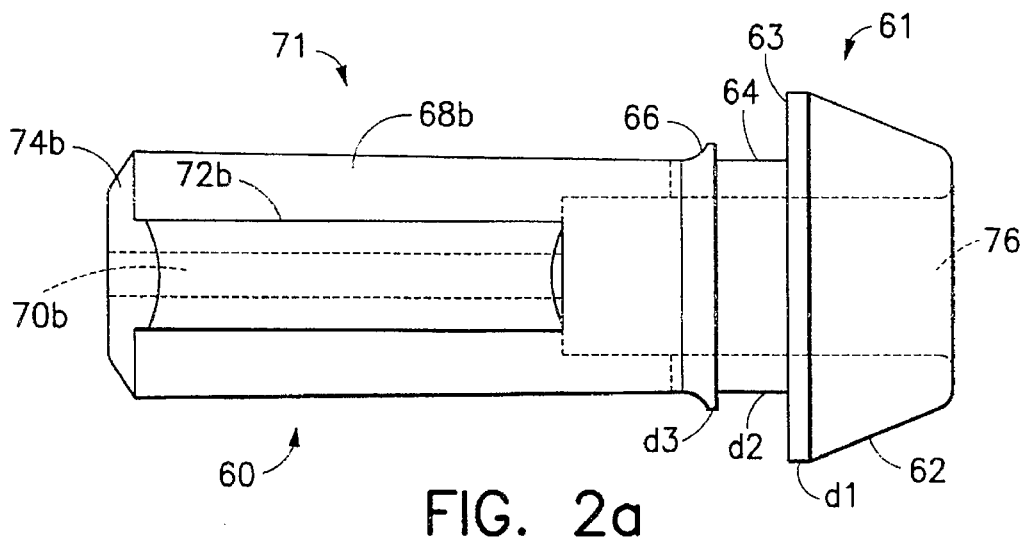
FIG. 2a is a top view of the collar of FIG. 2.
Figure 2B:
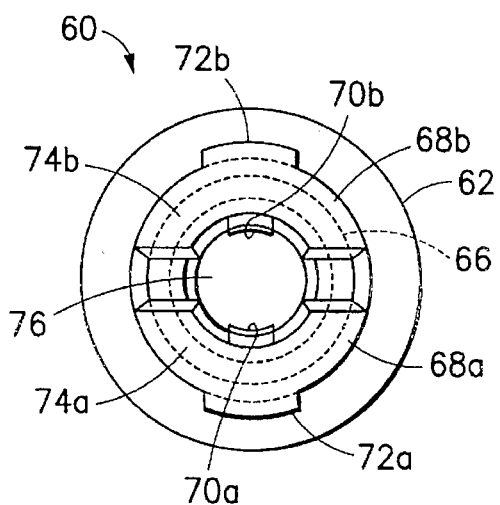
FIG. 2b is a proximal end view of the collar of FIG. 2.
Figure 2C:
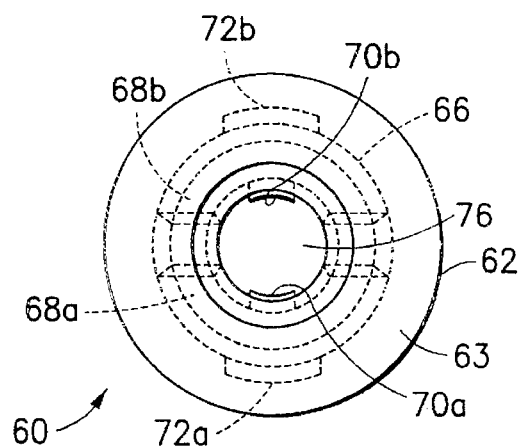
FIG. 2c is a distal end view of the collar of FIG. 2.

According to the invention, the actuator mechanism 18 is coupled to the coil 12 by means of a snap-fit collar 60 which is seen in detail in FIGS. 2 through 2c. In particular, the snap-fit collar 60 according to the invention is a molded, resilient plastic, substantially cylindrical member having first and second end portions 61, 71. A frustroconical tip 62 on a first end of the collar defines a stop flange 63 near the first end of the collar. A tapered locking flange 66, which is spaced apart from the stop flange 63 defines a narrow waist or groove 64 lying between the stop flange 63 and the locking flange 66. As seen in FIGS. 2 and 2a, the tip 62 flares diametrically outward from the first end of the collar to a first diameter "d1", and the narrow waist or groove 64 has a second diameter "d2" which is smaller than the first diameter "d1". The tapered locking flange 66 is substantially frustroconical and tapers diametrically inward toward the second end 71 of the collar from a third diameter "d3" which is larger than the second diameter "d2".

Extending from the first portion 61 of the collar 60 are a pair of substantially semi-cylindrical resilient cantilevered legs 68a, 68b which constitute the second portion 71 of the collar 60. The cantilevered legs 68a, 68b diverge slightly from each other as they extend away from the first portion 61 of the collar 60. The inner surface of each leg 68a, 68b is preferably rounded and provided with a plurality of coil engaging ribs 70a, 70b for engaging the coil 12 as will be described hereinafter. The outer surface of each leg 68a, 68b is preferably provided with a raised longitudinal key 72a, 72b for preventing rotation of the collar 60 in the handle 22. The free end 74a, 74b of each leg 68a, 68b is preferably tapered radially to facilitate insertion of the collar into the handle. The collar 60 is provided with a throughbore 76 which extends through the first end portion 61 of the collar 60 to the space 67 between the legs 68a, 68b. The throughbore 76 is provided in order to permit the coil 12 to pass into the space 67 between the legs 68a, 68b.

Referring now to FIGS. 3 and 3a, an endoscopic instrument actuator 18 for use with the snap-fit collar 60 includes a throughbore 32 having a diameter substantially the same as or slightly larger than the above-defined third diameter "d3", and a distal step or protrusion 33 defining an opening having a diameter substantially the same as or slightly larger than the above-defined second diameter "d2". The distal step is preferably provided with a pair of diametrically opposed keyways 35, 37 which extend into at least a portion of the wall 31 which defines the throughbore 32.

Figure 5:
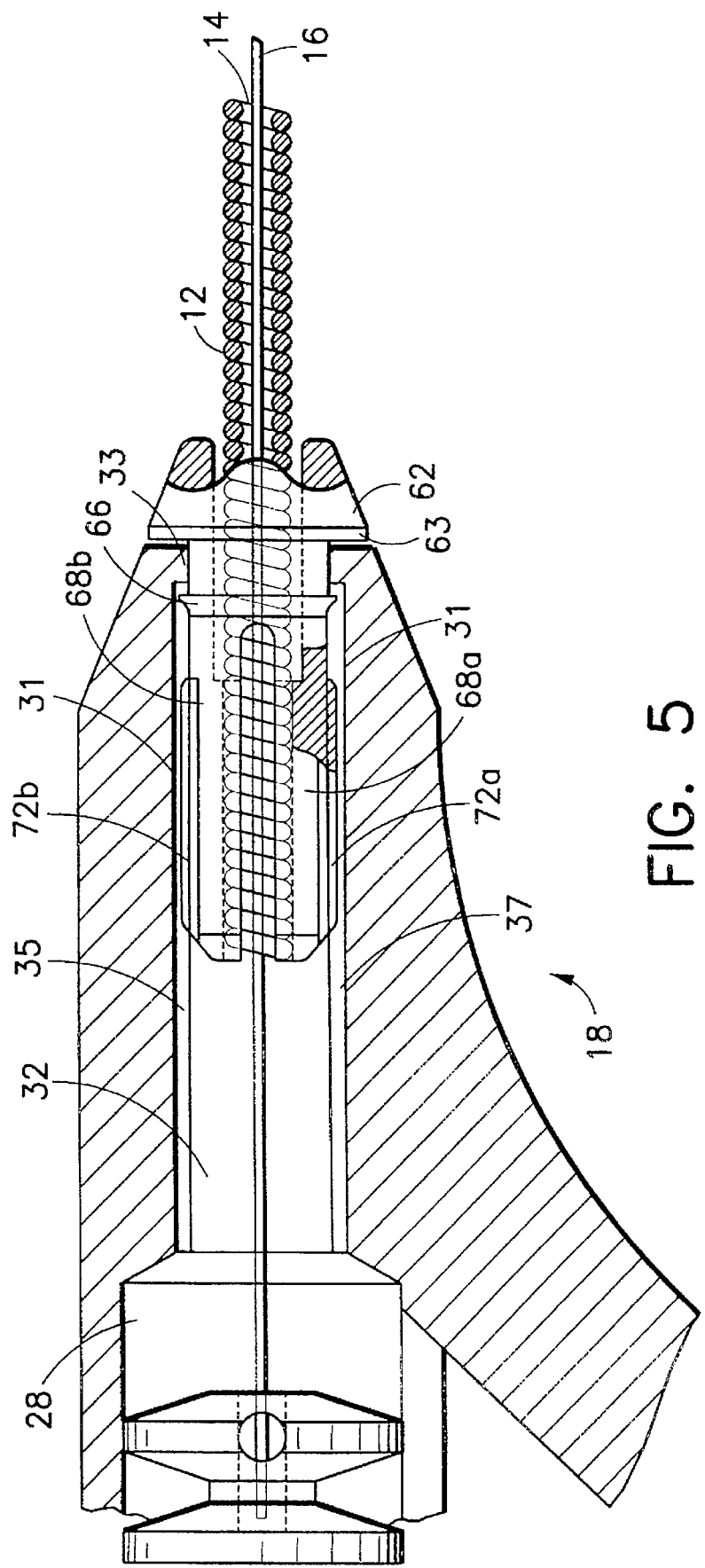
FIG. 5 is an enlarged broken side elevation view, partially transparent and in partial section, of the coil and collar assembly of FIG. 4 attached to the actuator according to the invention.

FIGS. 4 and 5 show how the collar 60, the coil 12, and the actuator handle 18 are assembled. As shown in FIG. 4, the snap-fit collar 60 fits easily over the flexible coil 12 so that the second end of the collar 60 is substantially aligned with the proximal end of the coil. As seen in FIG. 5, the collar 60 and coil 12 assembly is inserted into the distal end of the throughbore 32 of the actuator 18 with the keys 72a, 72b on the legs 68a, 68b of the collar 60 engaging the keyways 35, 37 of the distal step 33 in the throughbore of the actuator. As the cantilevered legs 68a, 68b enter the throughbore 32 of the actuator they are forced radially inward towards each other with their inner coil engaging ribs engaging and pressing into the coil 12 and spaces between the turns of the flexible coil. As a result, the ribs are deformed by the coil. As the collar and coil assembly is further advanced into the throughbore of the actuator, the locking flange portion 66 passes over the distal step or protrusion 33 in the actuator throughbore. Since the locking flange portion is tapered toward the second end of the collar, and the collar is made of resilient plastic, the locking flange is slightly deformed as it passes through the step into the throughbore of the actuator but returns to substantially its original shape after it passes through the step. Since the distal diameter of the locking flange portion is larger than the diameter of the opening defined by the step 33, the collar is prevented from moving distally over the step. Similarly, the stop flange 63 prevents the collar 60 from further movement into the throughbore 32. The keyways in the step portion preferably extend into the wall 31 of the throughbore a sufficient length so that the keys 72a, 72b on the legs of the collar reside in the keyways and prevent the collar from rotating in the handle.

Turning now to FIG. 6, an alternate collar 160 according to the invention is substantially the same as the collar 60 described above with reference to FIGS. 1–5, except for the tip portion 162. In this embodiment of the collar 160, the tip portion 162 extends over a substantial portion of the coil 12 to provide a strain relief at the distal end of an actuator.

As mentioned above, and as shown in FIG. 7, a snap-fit collar 260 according to the invention can be used to couple the distal end of the coil 12 to an end effector assembly 200. The collar 260 is substantially the same as the collar 60 described above, albeit perhaps smaller in overall size. The end effector assembly 200 includes a clevis member 202 and a pair of opposed jaws 204, 206. The clevis member 202 has a pair of clevis arms 208, 210 between which the jaws 204, 206 are rotatably mounted and a tube portion 212 which extends proximally from the clevis arms 208, 210. The tube portion 212 has a throughbore 214, a proximal protrusion or step 216, and a pair of diametrically opposed keyways 218, 220 which extend through the step and into the wall of the throughbore. The operation of the snap-fit collar 260 and its coupling with the tube portion 212 of the clevis member 202 is substantially the same as the operation and coupling of the collar 60 and actuator 18 described above.

There have been described and illustrated herein several embodiments of a snap-fit collar for coupling the end of a flexible coil to the actuator or the clevis of an endoscopic surgical instrument. While particular embodiments of the invention have been described, it is not intended that the invention be limited thereto, as it is intended that the invention be as broad in scope as the art will allow and that the specification be read likewise. Thus, while particular materials have been disclosed, it will be appreciated that other materials could be utilized. Also, while a particular endoscopic instrument actuator and clevis have been shown, it will be recognized that other types of actuators and clevis could be used with the snap-fit collar with similar results obtained. For example, the snap-fit collar can be used with a conventional "spool and thumb ring" handle typically used with endoscopic biopsy forceps. Moreover, while particular configurations have been disclosed in reference to the keys and keyways, it will be appreciated that other configurations could be used as well. Furthermore, while the collar has been disclosed as having a frustroconical tip, it will be understood that different shaped tips can achieve the same or similar function as disclosed herein. In addition, while the collar has been shown and described as substantially cylindrical, it is possible to make the exterior of the collar non-cylindrical so long as it fits into the throughbore of a handle or clevis substantially as described herein. It will therefore be appreciated by those skilled in the art that yet other modifications could be made to the provided invention without deviating from its spirit and scope as so claimed.

We claim:

1. A snap-fit collar for coupling the end of a flexible coil to a portion of an endoscopic surgical instrument having a throughbore with a protrusion defining a reduced diameter portion of the throughbore, said collar comprising:

a) a first end portion having an interior passage, an exterior stop flange with a first diameter and a resilient exterior tapered locking flange spaced apart from said stop flange and defining a groove lying between said stop flange and said locking flange, said groove having a second diameter which is smaller than said first diameter and being adapted to receive the protrusion, said tapered locking flange being tapered radially inward from a third diameter which is larger than said second diameter and being adapted to move through the reduced diameter portion in one direction only; and b) a second end portion extending from said first end portion and having a pair of cantilevered legs which diverge as they extend away from said first end portion, each of said legs having a plurality of coil engaging ribs on an inner surface thereof, and said legs defining a space which is in communication with said interior passage, said space and said interior passage being adapted to receive the end of the flexible coil, wherein when the end of the flexible coil is inserted through said interior passage into said space and said collar with the coil is inserted into the throughbore of the portion of the endoscopic surgical instrument, said legs are pressed toward each other and engage the coil with said ribs, said locking flange passes through the reduced diameter portion and said stop flange stops said collar from entering farther into the throughbore of the portion of the endoscopic surgical instrument.

2. A collar according to claim 1, wherein:
said first end portion has a substantially frustroconical part defining said stop flange.

3. A collar according to claim 1, wherein:
each of said legs has an outer surface with a raised key thereon.

4. A collar according to claim 1, wherein:
each of said legs has a radially tapered free end.

5. A collar according to claim 1, wherein:
said first end portion includes a stress relieving part which extends over part of the coil outside of the portion of the endoscopic surgical instrument.

6. An endoscopic surgical instrument, comprising:

a) a proximal actuator having a throughbore with a distal step defining a reduced diameter portion of said throughbore;

b) a flexible coil having a proximal end and a distal end;

c) a snap-fit collar having a pair of spaced apart radial flanges, an axial throughbore, and a pair of cantilevered legs, wherein the proximal end of said flexible coil is coupled to said proximal actuator by said snap-fit collar with said proximal end of said flexible coil residing in said axial throughbore of said collar, said pair of cantilevered legs residing in said throughbore of said proximal actuator and said spaced apart flanges residing on opposite sides of said distal step.

7. An endoscopic instrument according to claim 6, wherein:

said pair of spaced apart flanges comprises a first stop flange and a resilient second locking flange, said second locking flange being radially tapered so that said collar is snapped into said throughbore of said actuator by moving said locking flange through said reduced diameter portion of said throughbore.

8. An endoscopic instrument according to claim 7, wherein:

each of said pair of legs is inclined radially outward and has a radially tapered free end.

9. An endoscopic instrument according to claim 8, wherein:

each of said pair of legs has a plurality of coil engaging ribs on an inner surface thereof.

10. An endoscopic instrument according to claim 8, wherein:

each of said pair of legs has a raised key on an outer surface thereof, and said distal step and said throughbore in said actuator have a pair of diametrically opposed keyways which are engaged by said raised keys.

11. An endoscopic surgical instrument, comprising:

a) a proximal actuator;

b) a flexible coil having a proximal end and a distal end, said proximal end of said flexible coil being coupled to said proximal actuator;

c) a distal clevis having a proximal tube portion with a throughbore and a proximal step defining a reduced diameter portion of said throughbore; and d) a snap-fit collar having a pair of spaced apart radial flanges, an axial throughbore, and a pair of cantilevered legs, wherein the distal end of said flexible coil is coupled to said distal clevis by said snap-fit collar with said distal end of said flexible coil residing in said axial throughbore of said collar, said pair of cantilevered legs residing in said throughbore of said distal clevis and said spaced apart flanges residing on opposite sides of said proximal step.

12. An endoscopic instrument according to claim 11, wherein:

said pair of spaced apart flanges comprises a first stop flange and a resilient locking flange, said resilient locking flange being radially tapered so that said collar is snapped into said throughbore of said clevis by moving said locking flange through said reduced diameter portion of said throughbore over said proximal step.

13. An endoscopic instrument according to claim 12, wherein:

each of said pair of legs is inclined radially outward and has a radially tapered free end.

14. An endoscopic instrument according to claim 12, wherein:

each of said pair of legs has a plurality of coil engaging ribs on an inner surface thereof.

15. An endoscopic instrument according to claim 12, wherein:

each of said pair of legs has a raised key on an outer surface thereof, and said proximal step and said throughbore in said clevis have a pair of diametrically opposed keyways which are engaged by said raised keys.

16. A snap-fit collar for coupling an end of a flexible coil to a portion of an endoscopic surgical instrument having a throughbore with a step defining a reduced diameter portion of the throughbore, said collar comprising:

a substantially cylindrical member having an axial throughbore and a first and second end;

said first end having a pair of spaced apart radial flanges;

said second end being split and defining a pair of cantilevered legs with a space therebetween, wherein when the end of the flexible coil is inserted through said axial throughbore into the space between said legs and said collar with the coil is inserted into the throughbore of the portion of the endoscopic instrument, the coil is engaged by an inner surface of each of said legs and said collar is engaged by the throughbore of the portion of the endoscopic surgical instrument with said spaced apart flanges engaging the step in the throughbore of the portion of the endoscopic surgical instrument.

17. A snap-fit collar according to claim 16, wherein:

said radial flange closest to said legs is tapered radially inward toward said legs.

18. A snap-fit collar according to claim 17, wherein:

each of said legs has a plurality of coil engaging ribs on an inner surface thereof.

19. A snap-fit collar according to claim 18, wherein:

each of said legs is inclined radially outward toward said second end of said substantially cylindrical member.

20. A snap-fit collar according to claim 19, wherein:

each of said legs has a radially tapered free end.

21. A method of attaching an end of a flexible coil to one of a handle and a clevis of an endoscopic instrument, the handle and the clevis having a throughbore, said method comprising:

a) providing a collar with an axial bore for receiving the end of the coil;

b) inserting the coil into the axial bore of the collar;

c) inserting the collar with the end of the coil into the throughbore of the one of the handle and the clevis of the endoscopic instrument so that the collar is deformed radially and engages the end of the coil frictionally.

\* \* \* \* \*